US008376934B2

(12) United States Patent
Takahashi et al.

(10) Patent No.: US 8,376,934 B2
(45) Date of Patent: Feb. 19, 2013

(54) MULTIJOINT MANIPULATOR AND ENDOSCOPE SYSTEM HAVING THE SAME

(75) Inventors: Kazuhiko Takahashi, Hachioji (JP); Toshio Nakamura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 138 days.

(21) Appl. No.: 13/092,702

(22) Filed: Apr. 22, 2011

(65) Prior Publication Data

US 2011/0257480 A1 Oct. 20, 2011

Related U.S. Application Data

(63) Continuation of application No. PCT/JP2010/069312, filed on Oct. 29, 2010.

(30) Foreign Application Priority Data

Nov. 10, 2009 (JP) .................................. 2009-257319

(51) Int. Cl.
 *A61B 1/00* (2006.01)
 *A61B 1/04* (2006.01)
 *G06F 3/033* (2006.01)
(52) U.S. Cl. ......... 600/106; 600/118; 345/184; 345/161
(58) Field of Classification Search .................. 600/106, 600/118, 109, 117, 146, 182, 152, 407; 345/184, 345/161, 156, 157; 606/205, 130
See application file for complete search history.

(56) References Cited

U.S. PATENT DOCUMENTS

| 6,270,453 | B1 * | 8/2001 | Sakai .............................. 600/141 |
| 6,660,920 | B2 * | 12/2003 | Osuga ............................. 84/439 |
| 2002/0124712 | A1 * | 9/2002 | Osuga ............................. 84/454 |
| 2008/0221592 | A1 * | 9/2008 | Kawai ............................ 606/130 |
| 2009/0326319 | A1 | 12/2009 | Takahashi et al. |

FOREIGN PATENT DOCUMENTS

| EP | 2 108 327 A1 | 10/2009 |
| JP | A-6-31662 | 2/1994 |
| JP | A-2008-212349 | 9/2008 |

OTHER PUBLICATIONS

Feb. 3, 2012 European Search Report issued in Application No. 10 82 9853.0.

(Continued)

*Primary Examiner* — John P Leubecker
*Assistant Examiner* — Ronald D Colque
(74) *Attorney, Agent, or Firm* — Oliff & Berridge, PLC

(57) ABSTRACT

A multijoint manipulator apparatus includes a tubular-member, linear-motion-transmission-members, a drive-unit, a position-detector, a tension-detector, an operation-unit, and a movement-degree-calculation-unit. The linear-members are inserted in the tubular-member, one end and the other end of each of the linear-members being fixed to the vicinity of a joint of the tubular-member and the drive-unit, respectively. The drive-unit moves the linear-members. The position-detector and the tension-detector detect positions and tension of the linear-members, respectively. A desired position/posture of a point of interest is input to the operation-unit. The calculation-unit calculates a current position/posture of the point, a weighting factor serving to give priority to and move the linear-members the tension of which is relatively low among the linear-members, and movement degrees of the linear-members to move the point to the desired position/posture, and causes the drive-unit to pull the linear-members.

5 Claims, 7 Drawing Sheets

OTHER PUBLICATIONS

Ma et al., "Dynamic Control Approaches for a Coupled Tendon-Driven Manipulator," Transactions of the Japan Society of Mechanical Engineers (Book C), 1995, pp. 4359-4364, vol. 61—No. 591 (with Abstract).

Hirose et al., "Development of Tendon Driven Multi-Joint Manipulator Based on Coupled Drive," Transactions of the Society of Instrument and Control Engineers, 1990, pp. 1291-1298, vol. 26—No. 11 (with Abstract).

International Search Report dated Nov. 22, 2010 issued in International Patent Application No. PCT/JP2010/069312 (with translation).

* cited by examiner

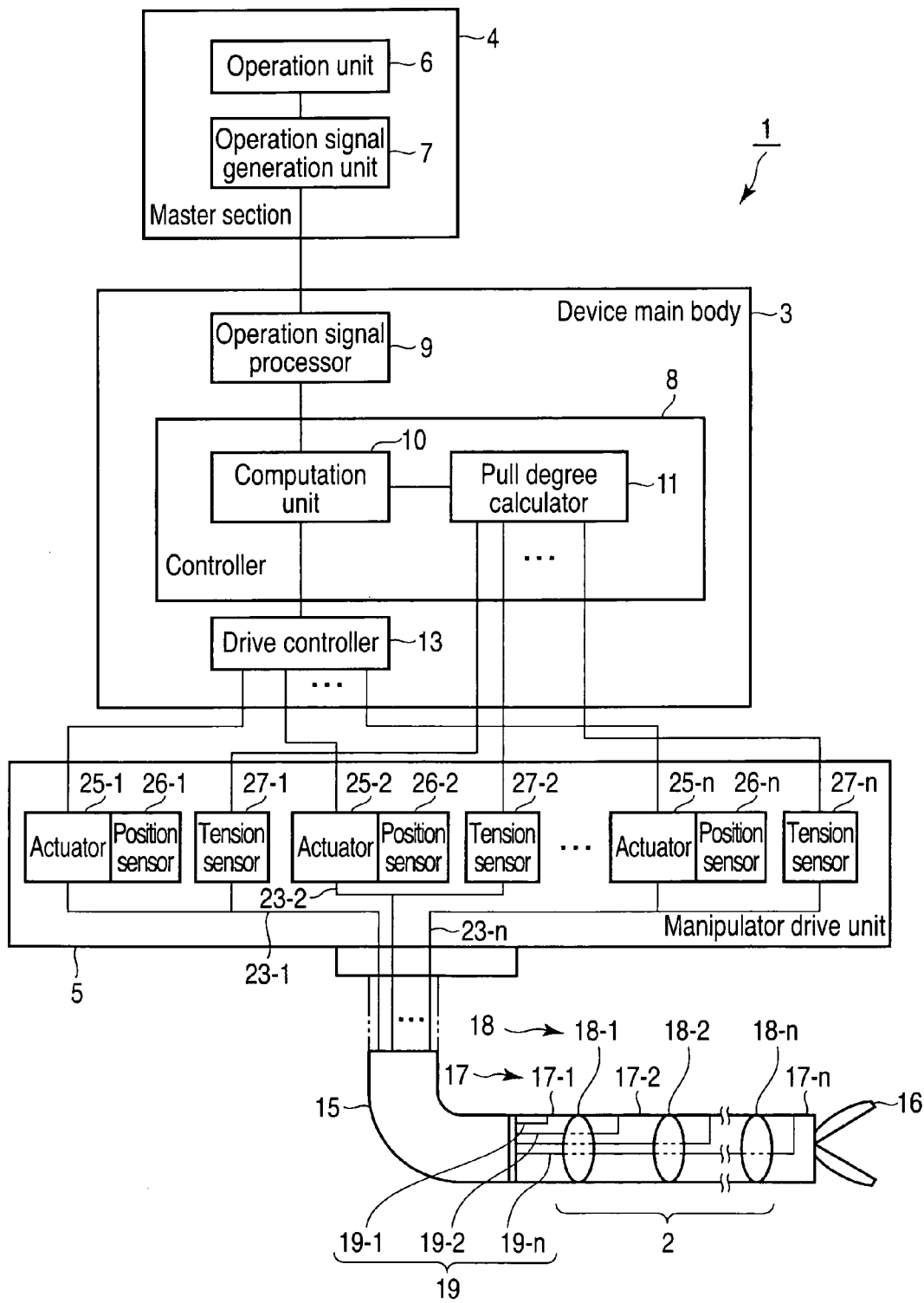
F I G. 1

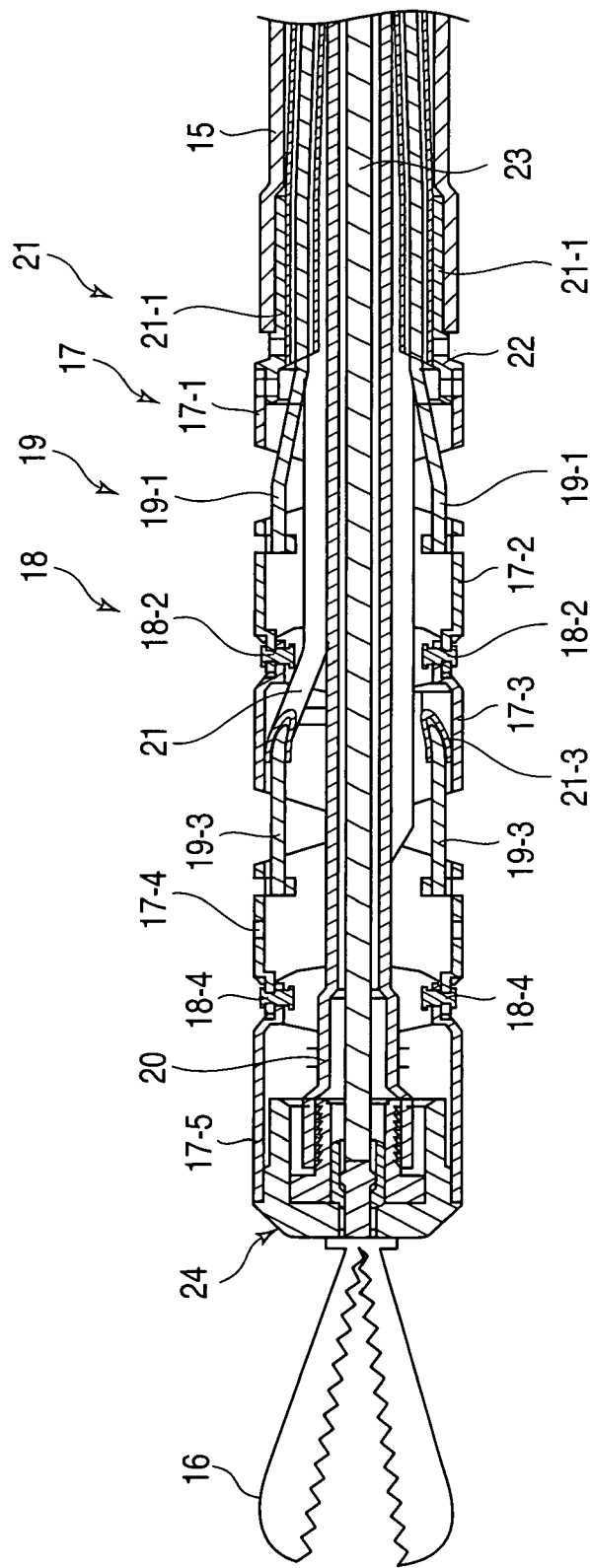
F I G. 2B

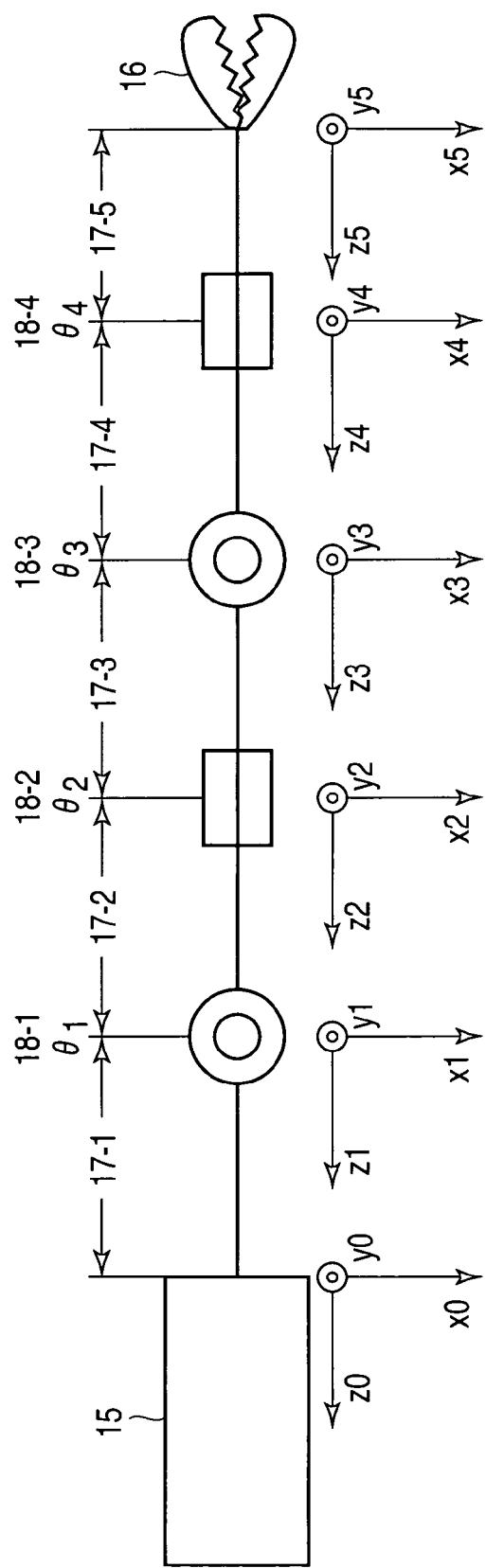
F I G. 3A

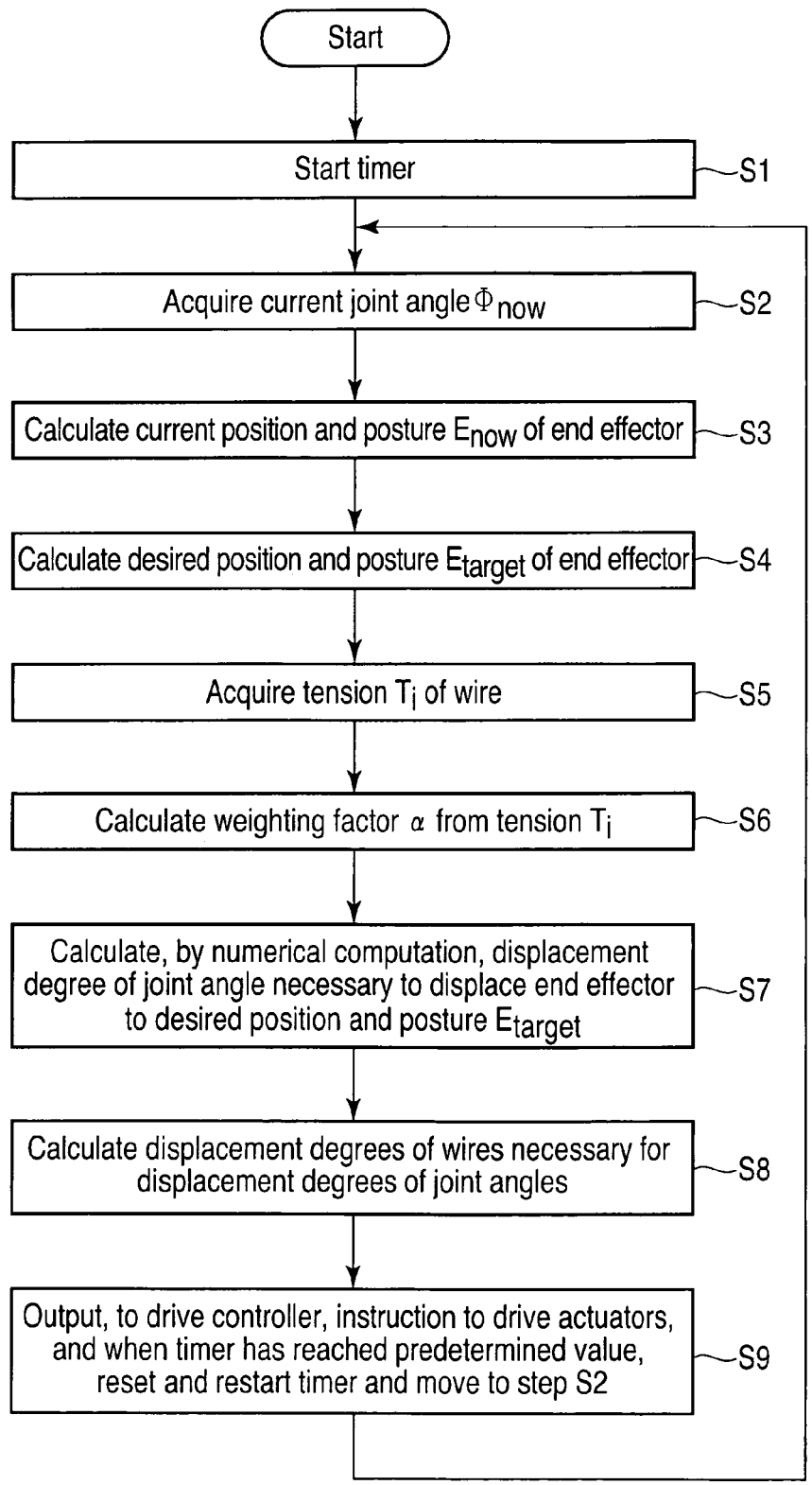
F I G. 4

MULTIJOINT MANIPULATOR AND ENDOSCOPE SYSTEM HAVING THE SAME

CROSS REFERENCE TO RELATED APPLICATIONS

This is a Continuation Application of PCT Application No. PCT/JP2010/069312, filed Oct. 29, 2010, which was published under PCT Article 21(2) in Japanese.

This application is based upon and claims the benefit of priority from prior Japanese Patent Application No. 2009-257319, filed Nov. 10, 2009, the entire contents of which are incorporated herein by reference.

BACKGROUND OF THE INVENTION

1. Field of the Invention

The present invention relates to a multijoint manipulator which flexes joints by pulling wires, and an endoscope system having the same.

2. Description of the Related Art

A manipulator in which rods are joined by flexible joints is generally known as one arm-type robot. Various functional parts are attached to the distal end of such a manipulator in use depending on the purpose. A functional part can be, for example, a holder for holding an article. Inside the manipulator, wires coupled on one end to the joints are provided for flexing motion. As at least two wires are required for one joint, at least the number of wires twice the number of joints is required.

According to a configuration known as a technique for reducing the manipulator in weight, wires are wound and hung around a pulley so that the wires interfere with one another, thereby reducing the number of wires. Control of such a manipulator that uses wires requires a joint torque control system and a wire tension control system and is complex. For example, a technique that performs the following control is disclosed in Jpn. Pat. Appln. KOKAI Publication No. 6-31662. According to this technique, a desired position for the displacement of the wires is first calculated from a target position of the distal end of the manipulator to be moved. Actual displacement of the wires is also measured. The desired position for the displacement of the wires is then compared with the actual displacement, and tension to be applied to the wires is found on the basis of the comparison to drive and control the manipulator.

BRIEF SUMMARY OF THE INVENTION

According to an aspect of the invention, a multijoint manipulator apparatus includes a tubular member which includes joints; linear motion transmission members inserted in the tubular member, one end of each of the linear motion transmission members being fixed to vicinity of one of the joints; a drive unit which longitudinally moves the linear motion transmission members to flex the tubular member, the other end of each of the linear motion transmission members being fixed to the drive unit; a position detector which detects positions of the linear motion transmission members moved by the drive unit; a tension detector which detects tension applied to the linear motion transmission members; an operation unit to which a desired position and a desired posture of a point of interest of the tubular member or a member attached to the tubular member are input; and a movement degree calculation unit, wherein the movement degree calculation unit calculates a current position and a current posture of the point of interest from the positions of the linear motion transmission members detected by the position detector, calculates a weighting factor based on the tension detected by the tension detector, the weighting factor serving to give priority to and move the linear motion transmission members the tension of which is relatively low among the linear motion transmission members, calculates, based on the weighting factor, movement degrees of the linear motion transmission members to move the point of interest from the calculated current position and the calculated current posture to the desired position and the desired posture, and causes the drive unit to pull the linear motion transmission members based on the movement degrees.

According to an aspect of the invention, an endoscope system includes a body cavity insertion unit which comprises the multijoint manipulator apparatus covered with an envelope, one end of the body cavity insertion unit is connected to the drive unit; an imaging unit provided at a distal end of the body cavity insertion unit opposite to said one end to which the drive unit is provided; an illuminator provided at the distal end of the body cavity insertion unit; and a display unit which displays an image captured by the imaging unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an example of the overall configuration of a multijoint manipulator apparatus according to a first embodiment of the present invention;

FIG. 2B is a diagram showing the general section of the configuration example of the multijoint manipulator according to the first embodiment of the present invention;

FIG. 3A is a diagram showing an example of the configuration, coordinates, and parameters of the multijoint manipulator according to the first embodiment of the present invention, and showing a general condition in which the manipulator is extended;

FIG. 4 is a flowchart showing an example of the operation processing of the multijoint manipulator apparatus according to the first embodiment of the present invention.

DETAILED DESCRIPTION OF THE INVENTION

[First Embodiment]

Figure 2A:
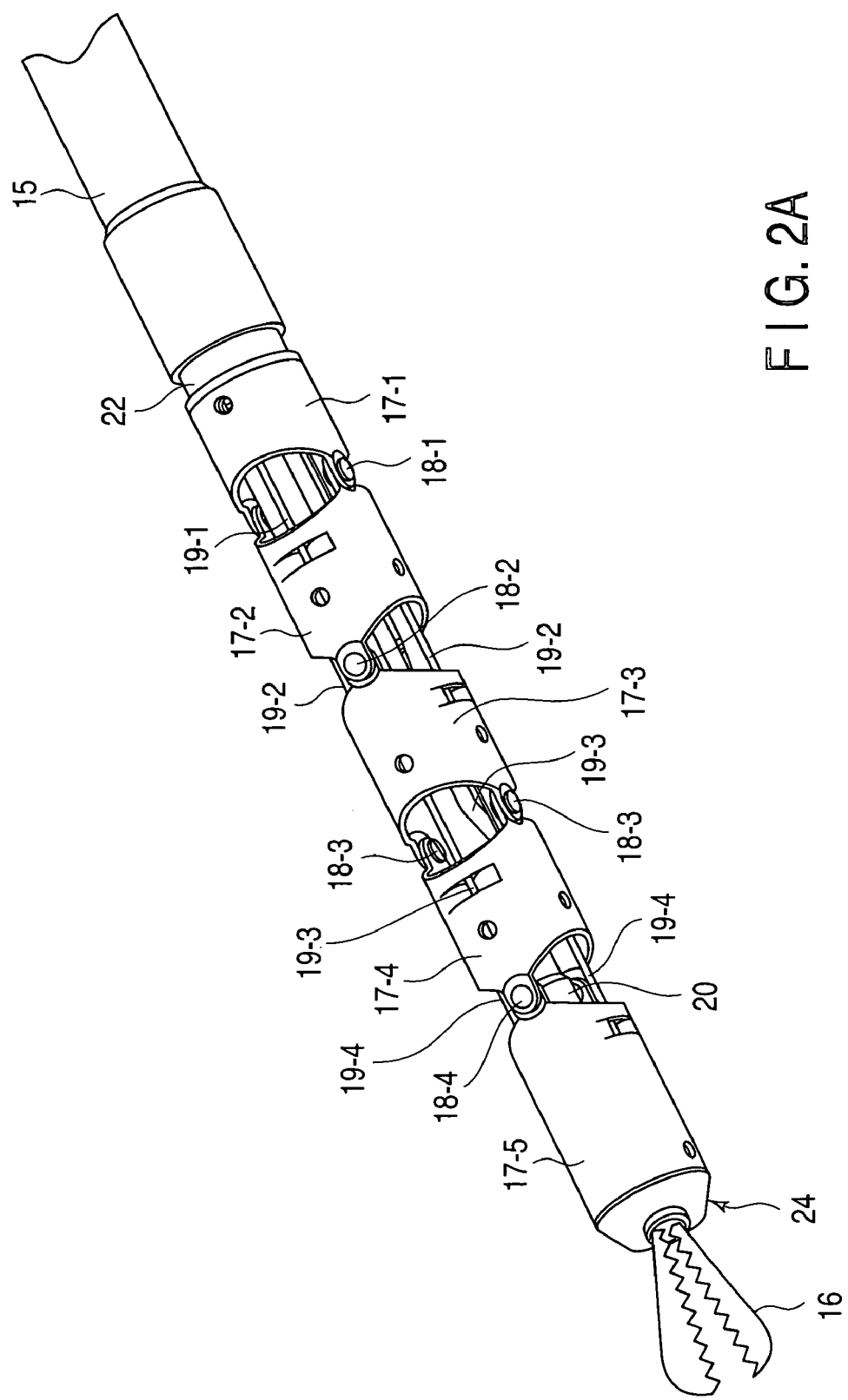
FIG. 2A is a diagram showing the general appearance of the configuration example of a multijoint manipulator according to the first embodiment of the present invention.

Initially, a first embodiment of the present invention is described with reference to the drawings. A multijoint manipulator apparatus 1 according to the present embodiment is a master-slave device. As shown in FIG. 1, the multijoint manipulator apparatus 1 generally comprises a multijoint manipulator 2, a device main body 3 for driving and controlling the multijoint manipulator 2, a master section 4 for generating an operation signal corresponding to the degree of user operation, and a manipulator drive unit 5 for driving the multijoint manipulator 2.

The general appearance of the multijoint manipulator 2 is shown in FIG. 2A, and the general section of the multijoint manipulator 2 is shown in FIG. 2B. As shown in FIGS. 2A and 2B, the multijoint manipulator 2 comprises a holder 16, cylindrical curving pieces 17 (17-1, 17-2, ..., 17-$n$), rivet-shaped pivot members 18 (18-1, 18-2, ..., 18-$n$), and wires (or angle wires) 19 (19-1, 19-2, ..., 19-$n$). The holder 16 is provided at the distal end of the multijoint manipulator 2. The rivet-shaped pivot members 18 (18-1, 18-2, ..., 18-$n$) flexibly join the curving pieces 17 together to form joints. One end of each of the wires 19 (19-1, 19-2, ..., 19-$n$) is fixedly attached by, for example, brazing to the vicinity of the joint of the curving piece 17. In response to the movement of the wires 19, the curving pieces 17 are rotated around the pivot members 18. The manipulator having four joints is shown by way of example in FIG. 2A and FIG. 2B. In the following explanation, the side of the multijoint manipulator 2 on which functional parts such as the holder 16 are mounted is the distal end, and the side fixed to, for example, a device is the proximal end. The multijoint manipulator 2 further comprises a flexible tube 15, a coupling member 22, and flexible coils 21 (21-1, 21-2, ..., 21-$n$). The flexible tube 15 is disposed on the proximal side of the multijoint manipulator 2, and is capable of elastically bending in a relatively flexible manner. The coupling member 22 couples the flexible tube 15 to the proximal curving piece 17-1. The flexible coils 21 (21-1, 21-2, ..., 21-$n$) are provided to penetrate from the curving pieces 17 to the proximal side of the flexible tube 15. Each of the respective wires 19 having one end fixed to the curving piece 17 is inserted through the flexible coil 21 (21-1, 21-2, ..., 21-$n$). An operation wire 23 for opening/closing the holder 16 for holding operation is inserted through a flexible tube 20 provided to penetrate from the curving pieces 17 to the proximal side of a flexible tube 12.

The joining form of the curving piece 17 and the pivot member 18 is described. On the distal side of each of the curving pieces 17 except for the curving pieces disposed on the distal and proximal sides of the multijoint manipulator 2, two tongue-shaped distal protrusions are provided across the cylindrical center of the curving piece. On the proximal side of this curving piece, two tongue-shaped proximal protrusions are provided across the cylindrical center of the curving piece in a direction perpendicular to (direction rotated 90 degrees relative to) the distal protrusions. The joining configuration of the curving pieces is, for example, as follows. As shown in FIG. 2A, the curving piece 17-2 and the curving piece 17-3 are rotatably joined together by laying holes made in the proximal protrusions of the curving piece 17-2 on holes made in the distal protrusions of the curving piece 17-3 and fitting the rivet-shaped pivot member 18 into the holes. In this way, the curving pieces 17 are joined together by the pivot members 18 on multiple stages in the form of a universal joint, thereby providing a joining form in which the angle in the front of the curving piece 17 is 90 degrees different from the angle in the rear.

In such a form of the universal joint in which the connection position of the curving piece 17 and the pivot member 18 alternately varies 90 degrees from each other, if one of a pair of wires 19 connected to the desired curving piece 17 is pulled, this curving piece 17 swings around two pivot members 18. Thus, the curving pieces 17 are freely flexed or extended in accordance with how much the wire 19 connected to the desired curving piece 17 is pulled, such that the holder 16 at the distal end of the multijoint manipulator 2 can be three-dimensionally displaced to a desired position and posture.

As shown in FIG. 1, the master section 4 comprises an operation unit 6 serving as an input component whereby a user inputs an operation instruction, and an operation signal generation unit 7 for generating an operation signal corresponding to the operation degree of the operation unit 6. The operation instruction issued by the master section 4 has a master-slave relationship with the multijoint manipulator 2, so that the multijoint manipulator 2 as the slave is curved in accordance with the operation instruction issued by the master section 4 as the master. The operation unit 6 is an input device such as a button switch, a joystick, a keyboard, or a mouse that is a general input instrument. For example, in the multijoint manipulator apparatus 1 comprising two manipulators, the operation unit 6 may be provided with two joysticks for the respective multijoint manipulators 2. The operation signal generation unit 7 generates an operation signal in accordance with the instruction input from the operation unit 6, and outputs the operation signal to the device main body 3.

The manipulator drive unit 5 comprises actuators 25 (25-1, 25-2, ..., 25-$n$) serving as drive sources of the wires 19, tension sensors 27 (27-1, 27-2, ..., 27-$n$) for detecting the tension applied to the respective wires 19, and position sensors 26 (26-1, 26-2, ..., 26-$n$) for detecting the displacements of the respective wires 19. Each of the actuators 25 has, by way of example, a motor (not shown) into which a rotation shaft is fitted in a pulley (not shown). As described above, at least two wires 19 are fixedly attached on one end to one curving piece 17. The other end of each of the wires 19 is coupled to or wound around the pulley. When the motor is turned, the pulley is turned, one of the wires 19 is pulled, and the other of the wires 19 is paid out. In response to such motion of the wires 19, the curving piece 17 is rotated around the pivot member 18.

The device main body 3 comprises a controller 8, an operation signal processor 9, and a drive controller 13. The operation signal processor 9 subjects the operation signal input from the operation signal generation unit 7 to various kinds of signal processing including digitization processing, and outputs the processed signal to the controller 8. The controller 8 includes a computation unit 10 and a pull degree calculator 11. The computation unit 10 performs computation concerning, for example, the control of each component of the multijoint manipulator apparatus 1. The pull degree calculator 11 calculates a pull degree of the wires 19 necessary for the distal end of the multijoint manipulator 2 to reach the desired position and posture indicated by the operator, in accordance with the tension of the wires 19 input from the tension sensors 27, the positions of the wires 19 input from the position sensors 26, and the operation instruction by the operator input from the computation unit 10. The pull degree calculator 11 outputs the calculated pull degree of the wires 19 to the computation unit 10. The computation unit 10 outputs this pull degree to the drive controller 13. The drive controller 13 controls the driving of the actuators 25 in accordance with the control signal which is input from the computation unit 10 and which is based on the pull degree of the wires 19.

In this way, for example, the multijoint manipulator 2 including the flexible tube 15, the curving pieces 17, the pivot members 18, the flexible coils 21, and the coupling member 22 functions as a tubular member which includes joints. For example, the wires 19 fixedly attached by, for example, brazing to the vicinities of the joints of the curving pieces 17 function as linear motion transmission members inserted in the tubular member, and one end of each of the linear motion transmission members is fixed to the vicinity of one of the joints. For example, the actuators 25 function as a drive unit which longitudinally moves the linear motion transmission members to flex the tubular member, and the other end of each of the linear motion transmission members is fixed to the drive unit. For example, the position sensors 26 function as a position detector which detects the positions of the linear motion transmission members. For example, the tension sensors 27 function as a tension detector which detects the tension applied to the linear motion transmission members. For example, the operation unit 6 functions as an operation unit to which a desired position and a desired posture of a part of interest of the tubular member or a member attached to the tubular member are input. For example, the pull degree calculator 11 functions as a movement degree calculation unit which calculates a current position and a current posture of the part of interest based on the positions of the linear motion transmission members detected by the position detector, and calculates movement degrees of the linear motion transmission members necessary to move the part of interest from the current position and posture to the desired position and the desired posture on the basis of the tension applied to the linear motion transmission members detected by the tension detector.

Figure 3B:
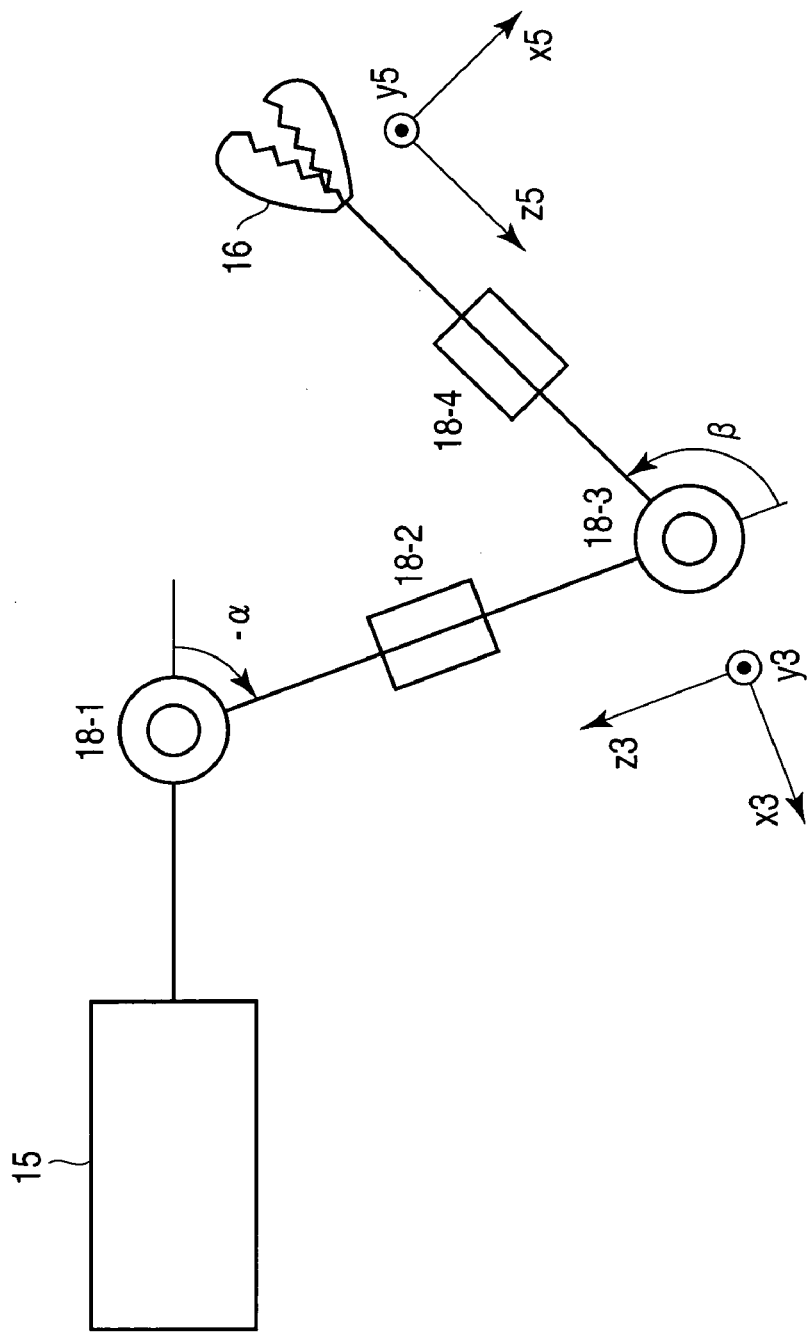
FIG. 3B is a diagram showing an example of the configuration, coordinates, and parameters of the multijoint manipulator according to the first embodiment of the present invention, and showing a general condition in which the manipulator is flexed.

Now, the flexing motion of the multijoint manipulator 2 having such a configuration is described. A multijoint structure model of the multijoint manipulator 2 having four pivoting joints is shown in FIG. 3A and FIG. 3B. Although there are four pivoting joints in the example described here for simplicity, it goes without saying that any number of joints may be used, and direct-acting joints, for example, may be used.

FIG. 3A shows a linearly extended condition of the multijoint manipulator 2. Five curving pieces 17-1 to 17-5 are arranged from the proximal side. The curving pieces 17-1 to 17-5 are joined by four pivot members 18-1 to 18-4. In the pivot member 18 of each axis, an x-axis, a y-axis, and a z-axis that are local and perpendicular to one another are set as shown in FIG. 3A. The pivot member 18-1 and the pivot member 18-3 pivot on the y-axis, and the pivot member 18-2 and the pivot member 18-4 pivot on the x-axis.

FIG. 3B shows an example of the multijoint manipulator 2 which is pivoted on the pivot member 18-1 and the pivot member 18-3 and which is flexed between the curving piece 17-1 and the curving piece 17-2 and between the curving piece 17-3 and the curving piece 17-4. In the example shown in FIG. 3B, a flexing angle $\theta_1$ of the pivot member 18-1 is $-\alpha$, and a flexing angle $\theta_3$ of the pivot member 18-3 is $\beta$.

Now, the processing performed in the controller 8 is described with reference to FIG. 4.

In step S1, the pull degree calculator 11 starts an unshown timer.

In step S2, using a relational expression between the displacement of the wire 19 and the joint angle of the multijoint manipulator 2, the pull degree calculator 11 calculates a current joint angle $\Phi_{now}$ of the multijoint manipulator 2 from the displacement of the wire 19 acquired by the position sensor 26. The joint angle $\Phi_{now}$ of the multijoint manipulator 2 having an n-degree of freedom is represented by Equation (1).

$$\Phi_{now} = (\theta_{1,now}, \theta_{2,now}, \ldots, \theta_{n,now})^T \qquad (1)$$

wherein $\theta_{1,now}, \theta_{2,now}, \ldots, \theta_{n,now}$ indicate the angles of a joint 1, a joint 2, . . . , a joint n, respectively.

In step S3, using a relational expression $E = A(\Phi)$ between a position and posture E and the joint angle $\Phi$, the pull degree calculator 11 calculates, by Equation (2), a current position and posture $E_{now}$ of an end effector such as the holder 16 at the distal end of the multijoint manipulator 2 on the basis of the current joint angle $\Phi_{now}$ calculated in step S2.

$$E_{now} = A(\Phi_{now}) = (x_{now}, y_{now}, z_{now}, \text{Roll}_{now}, \text{Yaw}_{now}, \text{Pitch}_{now})^T \qquad (2)$$

wherein $x_{now}, y_{now}, z_{now}, \text{Roll}_{now}, \text{Yaw}_{now}, \text{Pitch}_{now}$ indicate a current x-axis position, y-axis position, z-axis position, roll, yaw, and pitch of the end effector, respectively.

In step S4, the pull degree calculator 11 acquires, via the operation signal processor 9 and the computation unit 10, a desired position and posture $E_{target}$ of the end effector which are input by the operator using the operation unit 6 and generated in the operation signal generation unit 7. Here, the desired position and posture $E_{target}$ of the end effector are represented by Equation (3).

$$E_{target} = (x_{target}, y_{target}, z_{target}, \text{Roll}_{target}, \text{Yaw}_{target}, \text{Pitch}_{target})^T \qquad (3)$$

wherein $x_{target}, y_{target}, z_{target}, \text{Roll}_{target}, \text{Yaw}_{target}, \text{Pitch}_{target}$ indicate a desired x-axis position, y-axis position, z-axis position, roll, yaw, and pitch of the end effector, respectively.

In step S5, the pull degree calculator 11 acquires tension $T_i$ of the wire 19 for a joint i from the tension sensor 27. Here, i=1, 2, . . . , n.

In step S6, the pull degree calculator 11 calculates a weighting factor $\alpha$ on the basis of the tension $T_i$ by using Equation (4).

$$\alpha = (a_1, a_2, \cdots, a_n) \qquad (4)$$

$$a_1 = \frac{B_i T_{ave}}{T_i}$$

wherein $B_i$ indicates a constant number, and $T_{ave}$ indicates an average value of the all the tensions $T_i$.

In step S7, the pull degree calculator 11 calculates, by numerical computation, a displacement degree of a joint angle necessary to displace the end effector from the current position and posture $E_{now}$ to the desired position and posture $E_{target}$, that is, a joint angle displacement $\Delta\Phi$ that satisfies $E_{target} = A(\Phi_{now} + \Delta\Phi)$. A Jacobian matrix $J(\Phi)$ represented by Equation (5) is used for the numerical computation.

$$J(\Phi_j) = \begin{bmatrix} \frac{dx_j}{d\theta_1} & \frac{dx_j}{d\theta_2} & \cdots & \frac{dx_j}{d\theta_n} \\ \frac{dy_j}{d\theta_1} & \frac{dy_j}{d\theta_2} & \cdots & \frac{dy_j}{d\theta_n} \\ \frac{dz_j}{d\theta_1} & \frac{dz_j}{d\theta_2} & \cdots & \frac{dz_j}{d\theta_n} \\ \frac{dRoll_j}{d\theta_1} & \frac{dRoll_j}{d\theta_2} & \cdots & \frac{dRoll_j}{d\theta_n} \\ \frac{dYaw_j}{d\theta_1} & \frac{dYaw_j}{d\theta_2} & \cdots & \frac{dYaw_j}{d\theta_n} \\ \frac{dPitch_j}{d\theta_1} & \frac{dPitch_j}{d\theta_2} & \cdots & \frac{dPitch_j}{d\theta_n} \end{bmatrix} \quad (5)$$

First, in the numerical computation, the current position and posture $E_{now}$ are set in an initial value $E_1$. A calculation in Equation (6) is then repeated until the joint angle $\Phi$ converges.

$$\Phi_{j+1} = \Phi_j + J^{-1}(\Phi_j)(E_{target} - E_j)\alpha \quad (6)$$

A convergence value of the joint angle $\Phi$ thus obtained is the joint angle displacement $\Delta\Phi$ to be found. The joint angle displacement $\Delta\Phi$ is represented by Equation (7).

$$\Delta\Phi = (\Delta\theta_1, \Delta\theta_2, \ldots, \Delta\theta_n)^T \quad (7)$$

wherein $\Delta\theta_1, \Delta\theta_2, \ldots, \Delta\theta_n$ indicate the displacement degrees of the joint angles of the joint 1, the joint 2, ..., the joint n that are necessary to displace the end effector from the current position and posture $E_{now}$ to the desired position and posture $E_{target}$, respectively.

In step S8, the pull degree calculator 11 calculates displacement degrees of the respective wires that are necessary for the displacements $\Delta\theta_1, \Delta\theta_2, \ldots, \Delta\theta_n$ of the joint angles of the joint 1, the joint 2, ..., the joint n, respectively.

In step S9, the pull degree calculator 11 outputs, to the drive controller 13 via the computation unit 10, an instruction to drive each of the actuators 25 in accordance with the displacement degree of each of the wires calculated in step S8. The drive controller 13 actuates each of the actuators 25 in accordance with the instruction input from the computation unit 10. When the time of the timer started in S1 has reached a predetermined value, the pull degree calculator 11 resets and restarts the timer, and then moves to S2.

As a result of the operation described above, the wires 19 to which lower tension is applied are given priority and pulled among the multiple wires 19, and the end effector can be moved to the desired position and posture indicated by the operator. That is, in Equation (6) used in the numerical computation performed in step S7, the value of $\alpha$ set in step S6 and based on the tension applied to the wires 19 at the moment is considered. In this computation, the value of $\alpha$ has the effect of increasing the value of $\Delta\theta$ of the joints associated with the wires 19 to which lower tension is applied. Therefore, the value of $\alpha$ has the effect of decreasing the value of $\Delta\theta$ of the joints associated with the wires 19 to which higher tension is applied while the joints of the wires 19 to which lower tension is applied are given priority and moved. That is, the movement of the joints associated with the wires 19 to which higher tension is applied is inhibited. As a result, the possibility of damaging the wires 19 can be decreased.

When there is a tension $T_i$ that exceeds a preset threshold among the tensions $T_i$ of the wires 19 acquired in step S5; the value regarding this wire 19, among the weighting factors $\alpha$ calculated in step S6, may be set to 0 for control. That is, for example, when the tension applied to the wire 19-$x$ ($x$ is a natural number less than or equal to n) exceeds the preset threshold, the value of $a_x$ regarding the wire 19-$x$ in the weighting factor calculated in step S6 is set to 0. Accordingly, the value of $\Delta\theta_x$ of $\Delta\Phi$ obtained as a result of the numerical computation performed in step S7 becomes 0. That is, the pivot member 18-$x$ regarding the wire 19-$x$ is not used for the movement of the end effector. That is, the wire 19-$x$ is not pulled any more. While there is a possibility of damaging the wire 19, a further increase in the tension applied to this wire 19 can be avoided by adding the above-mentioned step. Consequently, the effect of preventing the damaging of the wire 19 can be further increased.

The acquisition of the current position and posture $E_{now}$ of the end effector by step S2 and step S3, the acquisition of the desired position and posture $E_{target}$ of the end effector by step S4, and the calculation of the weighting factor $\alpha$ by step S5 and step S6 may be carried out in any order. Thus, the order of these steps may be interchanged.

[Second Embodiment]

A second embodiment is described next with reference to the drawings. In the present embodiment, the multijoint manipulator apparatus according to the first embodiment described above is applied to a bending section of an endoscope main body in an endoscope system and to a bending driver of a surgical instrument provided in an endoscope.

Figure 5:
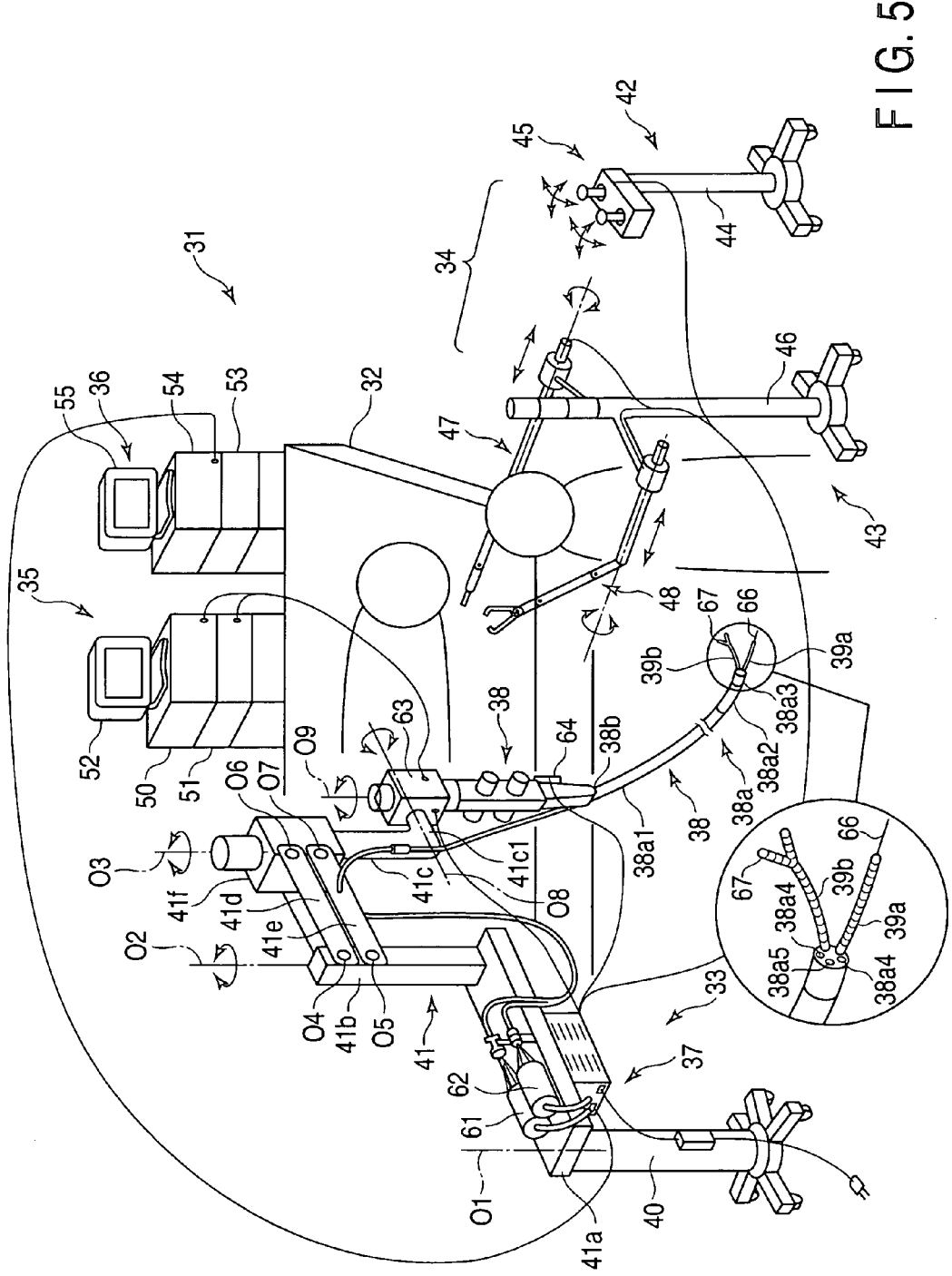
FIG. 5 is a diagram showing a configuration example of an endoscope system that uses a multijoint manipulator apparatus according to a second embodiment of the present invention.

FIG. 5 shows a configuration example of an endoscope system 31 according to the present embodiment that is installed in an operating room. An operating table 32 on which a subject lies supine is disposed in the center of the operating room. Provided in the vicinity of the operating table 32 are a diagnostic/surgical device 33 for diagnosing and treating a lesion in a body cavity, and an operating device 34 for the diagnostic/surgical device 33. In the vicinity of the opposite side of the operating table 32, an endoscope control device 35 and a surgical instrument control device 36 are provided to face the above-mentioned devices.

The diagnostic/surgical device 33 comprises an endoscope supporter 37, an endoscope 38 which is supported by the endoscope supporter 37 and which uses the above-described multijoint manipulator 2, and first and second active surgical instruments 39a and 39b. The first and second active surgical instruments 39a and 39b are multijoint structure robotics surgical instruments that use the above-described multijoint manipulator 2.

The endoscope supporter 37 comprises a floor stand 40 provided with rollers to be movable or fixable, and a multistage arm structure support arm 41 provided on the floor stand 40. The operating device 34 comprises an endoscope operating unit 42 for operating the endoscope 38, and a surgical instrument operating unit 43.

The endoscope operating unit 42 comprises a movable stand 44, and an endoscope controller 45 provided on the stand 44. The endoscope controller 45 has, for example, a joystick for operating the bending motion of the endoscope 38.

The surgical instrument operating unit 43 comprises a movable stand 46, and first and second instruction input units 47 and 48 provided on the stand 46. The first and second instruction input units 47 and 48 have a master-slave relationship (master-slave mode) with the first and second active surgical instruments 39a and 39b, and serve as masters. The first and second instruction input units 47 and 48 are master actuators of an arm mechanism having rods and joints.

The endoscope control device 35 comprises a light source unit 50, a display processor 51 as a camera control unit, and a display device 52. The surgical instrument control device 36 comprises an electric scalpel controller 53, a grip forceps controller 54, and a display unit 55 for control images of the first and second active surgical instruments 39a and 39b. A common monitor may be used for the endoscopic image display device 52 and the display unit 55 for the control images of the first and second active surgical instruments 39a and 39b.

The support arm 41 of the endoscope supporter 37 comprises a horizontal arm 41a, a first vertical arm 41b, a second vertical arm 41c, two (first and second) parallel link arms 41d and 41e, and an arm supporter 41f. The horizontal arm 41a has one end coupled to the upper portion of the floor stand 40 rotatably around a first vertical axis O1. The first vertical arm 41b has its lower end coupled to the other end of the horizontal arm 41a rotatably around a second vertical axis O2. The second vertical arm 41c is disposed parallel to the first vertical arm 41b. The first and second parallel link arms 41d and 41e are provided to lie between the first vertical arm 41b and the second vertical arm 41c. The arm supporter 41f supports the second vertical arm 41c rotatably around a third vertical axis O3. First and second active mechanisms 61 and 62 of the first and second active surgical instruments 39a and 39b are attached to the horizontal arm 41a.

One end of each of the first and second parallel link arms 41d and 41e is coupled to the upper end of the first vertical arm 41b rotatably around each of horizontal axes O4 and O5. The other end of each of the first and second parallel link arms 41d and 41e is coupled to the arm supporter 41f rotatably around each of horizontal axes O6 and O7. Thus, the first vertical arm 41b, the first and second parallel link arms 41d and 41e, and the arm supporter 41f form a parallelogram link which supports the second vertical arm 41c to be vertically movable in parallel.

A horizontally bent portion 41c1 is formed at the lower end of the second vertical arm 41c. An endoscope holder 63 is supported on the bent portion 41c1 rotatably around a horizontal axis O8. The proximal end of the endoscope 38 is removably supported on the endoscope holder 63 rotatably around a vertical axis O9.

The endoscope 38 comprises an elongate insertion portion 38a to be inserted into a body, and a hand-side end 38b coupled to the proximal end of the insertion portion 38a. The insertion portion 38a comprises an elongate flexible tubular portion 38a1, a bending section 38a2 which comprises the above-described multijoint manipulator 2 shown in FIG. 2A covered with an envelope and which is coupled to the distal end of the flexible tubular portion 38a1, and a known distal rigid portion 38a3 coupled to the distal end of the bending section 38a2.

One observation window, two illuminators 38a4, and two channel openings (not shown) for surgical instrument insertion are provided at the distal end of the distal rigid portion 38a3. An imaging unit 38a5 comprising optical system such as an objective lens and an image pickup device such as a CCD is provided inside the observation window. This imaging unit images, for example, a lesion in a body cavity. An image signal obtained in the imaging unit of the endoscope 38 is sent to the display processor 51 through a connection cable, and converted to a video signal. An image captured by the endoscope 38 is shown on the display device 52 by the video signal.

The bending section 38a2 is remotely bent by tilting the joystick of the endoscope controller 45. In this bending operation, as has been described in the first embodiment, wires to which lower tension is applied are given priority and pulled to flex curving pieces joined by pivot members. The bending of this bending section 38a2 allows a desired observation target (e.g., a lesion) to be captured in an observation field of view (or an imaging field of view).

Two channel openings in communication with two channels for surgical instrument insertion are formed in the vicinity of a coupling portion between the hand-side end 38b and the insertion portion 38a. The first and second active surgical instruments 39a and 39b that are respectively inserted from the proximal side of the endoscope extend from the channel openings. In the first and second active surgical instruments 39a and 39b, the multijoint manipulator 2 is used for the bending driver extending from the channel opening, as in the endoscope 38 described above. At the distal end of these parts, for example, an electric scalpel 66 and a grip portion 67 for gripping a lesion are attached as surgical instruments.

Although each of the first and second active surgical instruments 39a and 39b is inserted in each of the two insertion channels in the configuration shown in the present embodiment, multiple endoscopic surgical instruments may be inserted in one insertion channel. Moreover, the hand-side end 38b may be provided with a bending operation unit 64 such as a joystick or a cross key for bending the bending section 38a2.

In this way, for example, the bending section 38a2 functions as a body cavity insertion unit which comprises the multijoint manipulator apparatus covered with an envelope. For example, the imaging unit 38a5 functions as an imaging unit, and the body cavity insertion unit is provided with the drive unit at one end and the imaging unit at the other end. For example, the illuminator 38a4 functions as an illuminator provided at the other end of the body cavity insertion unit. For example, the display device 52 functions as a display unit which displays an image captured by the imaging unit. For example, the first active surgical instrument 39a and the second active surgical instrument 39b function as surgical instrument manipulators as the multijoint manipulator apparatuses. For example, the electric scalpel 66 and the grip portion 67 function as surgical instruments provided at the distal ends of the surgical instrument manipulators.

As described above, in the present embodiment, the multijoint manipulator 2 according to the present invention is used for the active bending section of the endoscope main body in the endoscope system and for an active robot arm (bending driver) of the surgical instrument. By using the multijoint manipulator 2 according to the present invention, wires to which lower tension is applied are given priority and pulled to drive and move the manipulator to a desired position and posture even if the operator operates without considering the wire tension. The wires to which lower tension is applied are given priority and used in this manner, such that the possibility of damaging the wires can be decreased.

Although the electric scalpel 66 and the grip portion 67 are provided at the distal ends of the active surgical instruments 39a and 39b in the example shown in the present embodiment described above, various other surgical instruments such as an ultrasonic wave emitting device may be used instead of the active electric scalpel or the grip portion.

As described above, the multijoint manipulator apparatus according to the present invention can be applied to the bending section of the endoscopic device and the curving driver of the robotics surgical instrument. In addition, the multijoint manipulator apparatus according to the present invention can also be applied to an arm mechanism of an industrial robot. For example, the multijoint manipulator apparatus according to the present invention can be installed in various robots; a robot for assembling industrial products such as automobiles, a remote-controlled robot for loading and conveying pellets of nuclear fuel in power plants, a robot for loading and unloading goods, and a carrying robot for moving and carrying goods in outer space. The multijoint manipulator apparatus according to the present invention can inhibit the damaging of the wires, and is therefore particularly advantageously used to drive a robot provided in a place remote from the operator.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multijoint manipulator apparatus comprising:
   a tubular member which includes joints;
   linear motion transmission members inserted in the tubular member, one end of each of the linear motion transmission members being fixed to vicinity of one of the joints;
   a drive unit which longitudinally moves the linear motion transmission members to flex the tubular member, the other end of each of the linear motion transmission members being fixed to the drive unit;
   a position detector which detects positions of the linear motion transmission members moved by the drive unit;
   a tension detector which detects tension applied to the linear motion transmission members;
   an operation unit to which a desired position and a desired posture of a point of interest of the tubular member or a member attached to the tubular member are input; and
   a movement degree calculation unit, wherein the movement degree calculation unit calculates a current position and a current posture of the point of interest from the positions of the linear motion transmission members detected by the position detector,
   calculates a weighting factor based on the tension detected by the tension detector, the weighting factor serving to give priority to and move the linear motion transmission members the tension of which is relatively low among the linear motion transmission members,
   calculates, based on the weighting factor, movement degrees of the linear motion transmission members to move the point of interest from the calculated current position and the calculated current posture to the desired position and the desired posture, and
   causes the drive unit to pull the linear motion transmission members based on the movement degrees.

2. The multijoint manipulator apparatus according to claim 1, wherein the movement degree calculation unit sets the movement degree of the linear motion transmission member to zero when the tension applied to the linear motion transmission member is greater than or equal to preset tension.

3. The multijoint manipulator apparatus according to claim 1, wherein the movement degree calculation unit calculates the movement degrees of the linear motion transmission members by a convergent numerical computation that uses a Jacobian matrix regarding a position and a posture of the point of interest and displacements of the joints.

4. An endoscope system comprising:
   a body cavity insertion unit which comprises the multijoint manipulator apparatus according to claim 1 covered with an envelope, one end of the body cavity insertion unit is connected to the drive unit;
   an imaging unit provided at a distal end of the body cavity insertion unit opposite to said one end to which the drive unit is provided;
   an illuminator provided at the distal end of the body cavity insertion unit; and
   a display unit which displays an image captured by the imaging unit.

5. An endoscope system comprising:
   a body cavity insertion unit which comprises the multijoint manipulator apparatus according to claim 1 covered with an envelope, one end of the body cavity insertion unit is connected to the drive unit;
   an imaging unit provided at a distal end of the body cavity insertion unit opposite to said one end to which the drive unit is provided;
   an illuminator provided at the distal end of the body cavity insertion unit;
   a display unit which displays an image captured by the imaging unit:
   a surgical instrument manipulator as the multijoint manipulator apparatus according to claim 1, the surgical instrument manipulator being inserted in the body cavity insertion unit and extending from the distal end of the body cavity insertion unit; and
   a surgical instrument provided at a distal end of the surgical instrument manipulator.

* * * * *